US012629012B2

(12) United States Patent
Juergens et al.

(10) Patent No.: US 12,629,012 B2
(45) Date of Patent: May 19, 2026

(54) METHOD FOR OPERATING THE HEATING SYSTEM OF AN ENDOSCOPE, HEATING SYSTEM OF AN ENDOSCOPE, AND ENDOSCOPE SYSTEM

(71) Applicant: OLYMPUS WINTER & IBE GMBH, Hamburg (DE)

(72) Inventors: Thorsten Juergens, Hamburg (DE); Sven Pabst, Giekau (DE); Sebastian Jungbauer, Hamburg (DE)

(73) Assignee: OLYMPUS WINTER & IRE GMBH, Hamburg (DE)

( * ) Notice: Subject to any disclaimer, the term of this patent is extended or adjusted under 35 U.S.C. 154(b) by 1011 days.

(21) Appl. No.: 17/399,198

(22) Filed: Aug. 11, 2021

(65) Prior Publication Data

US 2021/0369099 A1     Dec. 2, 2021

Related U.S. Application Data

(63) Continuation-in-part of application No. PCT/EP2020/052735, filed on Feb. 4, 2020.

(30) Foreign Application Priority Data

Feb. 11, 2019    (DE) .......................... 102019103291.1

(51) Int. Cl.
*A61B 1/12* (2006.01)
*A61B 1/00* (2006.01)

(52) U.S. Cl.
CPC .......... *A61B 1/127* (2013.01); *A61B 1/00027* (2013.01); *A61B 1/128* (2013.01); *A61B 2562/0271* (2013.01)

(58) Field of Classification Search
CPC ..... A61B 1/127; A61B 1/00027; A61B 1/128; A61B 2562/0271; G05D 23/1917; G05D 23/24
See application file for complete search history.

(56) References Cited

U.S. PATENT DOCUMENTS

2005/0092735 A1* 5/2005 Merk ................. G05D 23/1917
                                                              219/494
2013/0116507 A1* 5/2013 Segawa .................. A61B 1/045
                                                              600/109

(Continued)

FOREIGN PATENT DOCUMENTS

JP        2014-104037 A      6/2014

OTHER PUBLICATIONS

International Search Report dated Apr. 21, 2020 issued in PCT/EP2020/052735.

*Primary Examiner* — Michael J Carey
*Assistant Examiner* — Christen A Sharpless
(74) *Attorney, Agent, or Firm* — Scully, Scott, Murphy & Presser, P.C.

(57) ABSTRACT

A method for operating a heating system of an endoscope. The endoscope including a heating element and a temperature sensor in a distal region of the endoscope and a supply unit outside of the endoscope, the supply unit being connected to the heating element and the temperature sensor, wherein the supply unit activates and deactivates a power supply for the heating element on a basis of a temperature measurement value ascertained by the temperature sensor using two-state control, and a monitoring unit including a monitoring circuit which is powered by the power supply for the heating element. The method including: monitoring, with the monitoring circuit, the temperature sensor for a malfunction; and interrupting the power supply to the heating element if the malfunction of the temperature sensor is determined.

8 Claims, 3 Drawing Sheets

(56) References Cited

U.S. PATENT DOCUMENTS

| | | | |
|---|---|---|---|
| 2013/0261497 A1* | 10/2013 | Pertijs | A61B 5/6876 |
| | | | 600/549 |
| 2014/0221743 A1* | 8/2014 | Sugiyama | A61B 1/0676 |
| | | | 600/109 |
| 2016/0270629 A1* | 9/2016 | Kasumi | H02J 7/0044 |
| 2017/0112561 A1* | 4/2017 | Motai | A61F 5/0083 |
| 2018/0228357 A1* | 8/2018 | Fujii | A61B 1/127 |
| 2019/0059713 A1* | 2/2019 | Allen | B08B 1/14 |
| 2021/0369099 A1* | 12/2021 | Juergens | A61B 1/00027 |

\* cited by examiner

Fig. 1

METHOD FOR OPERATING THE HEATING SYSTEM OF AN ENDOSCOPE, HEATING SYSTEM OF AN ENDOSCOPE, AND ENDOSCOPE SYSTEM

CROSS-REFERENCE TO RELATED APPLICATION

The present application is a continuation-in-part application of PCT/EP2020/052735 filed on Feb. 4, 2020, which is based upon and claims the benefit to DE 10 2019 103 291.1 filed on Feb. 11, 2019, the entire contents of each of which are incorporated herein by reference.

BACKGROUND

Field

The present disclosure relates to a method for operating a heating system of an endoscope, which comprises a heating element and a temperature sensor in the distal region of the endoscope and a supply unit outside of the endoscope, the supply unit being connected to the heating element and the temperature sensor, wherein the supply unit activates and deactivates a power supply for the heating element on the basis of a temperature measurement value ascertained by means of the temperature sensor using two-state control, and a heating system and an endoscope system.

Prior Art

The present disclosure generally relates to surgical endoscopes and systems, specifically optical endoscopes that have an entrance window at the distal end of the endoscope shaft, which separates the internal space of the endoscope shaft with the optics situated behind it from the external space. The endoscope optics can be straight-view optics or sideways-view optics, with the light entering it being deflected in the direction of the endoscope shaft in the latter case. The light can then be guided further via relay systems to the proximal end of the shaft, or it can be captured directly behind the distal optical assembly by one or several image sensors which transmit electronic image signals to an evaluation and/or display unit.

Independently from the optics disposed behind the entrance window, it is necessary to adjust the distal part, such as the entrance window, to the body temperature of a patient before and during a use of the endoscope, since, due to the temperature difference between the ambient temperature and the temperature in a body cavity of the patient, the entrance window will fog up. A fogged-up entrance window, however, makes the examination to be performed with the endoscope impossible.

For this reason, modern endoscopes for surgical application have a heating element, a so-called actor, in the region of the distal tip, which can be near to the entrance window, which is energized in order to adjust the entrance window to the desired temperature, such as in the range of the human body temperature. In order to achieve and hold this temperature, a simple control system is provided, which comprises an external power supply by means of a supply unit as well as a temperature sensor in the immediate spatial vicinity of the heating element. The supply unit, which functions as a control unit in this case, is connected to the temperature sensor via a two-core conductor and is connected to the heating element via a further two-core conductor.

The control is typically implemented as a two-state control, wherein the energizing of the heating element is activated and deactivated on the basis of the temperature, which is measured by means of the temperature sensor. This control is normally provided with a hysteresis with respect to the switching temperature, such that the energizing is, for example, stopped when the temperature reaches 39° C. while heating up, and is restarted when the temperature drops below 35° C. In this manner, it is ensured that the temperature remains within the range of approx. ±1.5° C. to approx. ±2.5° C. of the body temperature of a human being without the power supply for the heating element being activated and deactivated too quickly. After the initial power-on of the heating system, a regular control operation establishes itself.

The functioning of this system depends on the temperature sensor functioning properly. For this purpose, thermistors are often used, which are supplied with a constant current by a constant current source. The voltage dropping across the thermistor is a measure for the temperature prevailing at the location of the thermistor. Thermistors develop various malfunctions as their operating duration increases. Thus, jumps, i.e., discontinuities, in the temperature curve of the resistor can develop, and the temperature curve can permanently change due to the increase in resistance. This is reflected by a faulty calibration and thus in faulty temperature measurements. In the case of thermistors with a negative temperature coefficient (NTC), which are usually used for the described application in heating systems of endoscopes and which conduct electricity better in the hot state than in the cold state, changes in the behavior of the thermistors have the effect that lower temperatures are measured than are actually prevalent. This means for the control of the heating system that the heating element is energized with more power in order to compensate for the temperature incorrectly sensed as being lower. Such excessive heating can result in an endangerment of the patient.

Such an endangerment of the patient must be avoided. To this end, endoscopes are checked regularly. However, it cannot be excluded that such a malfunction manifests gradually or during a treatment. A detection of malfunctions of the temperature sensor is therefore desirable. Furthermore, it is desirable that even existing endoscopes can be retrofitted.

One solution to this problem would be to use additional, redundant temperature sensors in the area of the heating element, so that malfunctions of individual temperature sensors could be detected by taking multiple measurements using the various temperature sensors and comparing them with each other and with previous measurements. The endoscopes and heating systems known from the state of the art, however, do not offer any simple options in this regard since the heating systems are not scalable. For example, it is not possible to accommodate further temperature sensors in the distal region of the endoscope, and even if further temperature sensors were to be received distally, the number of conductors would have to be increased, which requires a modification of the conductor interface, and the controller on the side of the supply unit would have to be modified in order to support the greater number of sensors.

SUMMARY

Conversely, it is an object to make the operation of the heating system of an endoscope with a heating element in the distal region safer.

Such object can be solved by a method for operating a heating system of an endoscope, which comprises a heating element and a temperature sensor in the distal region of the endoscope and a supply unit outside of the endoscope, the supply unit being connected to the heating element and the temperature sensor, wherein the supply unit activates and deactivates a power supply for the heating element on the basis of a temperature measurement value ascertained by means of the temperature sensor using two-state control, wherein the endoscope comprises a monitoring unit, such as one arranged in a proximal part of the endoscope, which comprises a monitoring circuit that is powered by means of the power supply for the heating element, wherein the monitoring circuit monitors the temperature sensor and interrupts the power supply to the heating element if a malfunction of the temperature sensor is determined.

Such method monitors the operation of the temperature sensor in a simple manner without having to modify or adapt the existing components of the heating system, namely the temperature sensor, the heating element and the supply unit. Instead, a monitoring unit is introduced, which can be accommodated in a more spacious part of the endoscope, such as in the proximal region thereof, for example in the handle, parasitically monitors the functioning of the temperature sensor, and intervenes if a malfunction of the temperature sensor is determined and interrupts the power supply to the heating element. This way, it is ensured that no situation will occur that is dangerous to a patient, which could, for example due to excessive heating, lead to burns or other damage.

Retrofitting with such a monitoring unit is possible in a simple manner for many endoscope types and requires no modifications on the supply unit, the temperature sensor, or the heating element. Since the monitoring unit itself is powered by the power supply for the heating element, it is only active when the heating element itself is being energized. It is possible to ensure effective monitoring of the temperature sensor function even in this case.

In one embodiment, the monitoring unit can comprise a monitoring temperature sensor connected to the monitoring circuit, wherein the monitoring circuit checks, whether the endoscope and/or the heating system was or respectively were newly activated after a break of a predefined length sufficient for the heating element to cool to an ambient temperature, or if only the energizing of the heating element was interrupted while the endoscope and the heating system continued to operate, wherein in the case of a new activation, the monitoring circuit compares temperature measurements of the temperature sensor and the monitoring temperature sensor with one another and, in case of a deviation of the temperature measurements beyond a predefined tolerance range, determines a malfunction of the temperature sensor.

In terms of measurement, this procedure means comparing the temperature measurements of two temperature sensors, namely the temperature sensor of the original heating system and the monitoring temperature sensor of the monitoring unit. In this way, redundancy of temperature measurement is established, albeit at a level of mutual calibration. Since the monitoring temperature sensor is disposed in a proximal region of the endoscope together with the monitoring unit, it is not in the immediate vicinity of the temperature sensor to be monitored and thus not directly thermally connected to it. For this reason, in order to compare the temperature measurements, it is necessary to first establish conditions or verify that such conditions exist, in which it can be assumed that both temperature sensors are at a similar temperature level so that the two temperature measurements can be compared. This is the case if the endoscope has not been used for a prolonged period of time and has therefore taken on the ambient temperature as a whole, both in the distal and in the proximal region. In that case, the measurements become comparable to one another and the temperature measurement of the monitoring temperature sensor can be used to verify the temperature measurement of the temperature sensor.

Since this state normally exists at the beginning of a treatment and before heating the distal region, this is also termed a "power-on detection" Immediately after the heating element has been switched on by the supply unit, the monitoring unit checks whether a sufficiently long time has elapsed or whether the endoscope has continued to operate without heating, which would also result in unsuitable conditions for a corresponding comparative measurement. For the time meters, the monitoring unit can encompass a time member, for example an RC member, which slowly discharges. The charge in this RC member must in this case drop below a predefined threshold before the condition of the sufficient idle time is fulfilled.

A second verification can take place with regard to the operation of the endoscope without energizing the heating element. If the monitoring unit or the monitoring circuit, respectively, comprises an energy accumulator which is charged via the conductor to the temperature sensor of the endoscope, a charged state can be interpreted to the effect that the endoscope was further operated.

A second fault characteristic of temperature sensors, such as thermistors, is that the temperature curve shows jumps. For example, the temperature curve can be nominal at room temperature, while a jump occurs during heating. This is not detected by the power-on detection. A further embodiment therefore provides that the monitoring circuit can monitor successive temperature measurements of the temperature sensor for jumps and, if a predefined temperature increase threshold, such as of 2° C./s, is exceeded, determines a malfunction of the temperature sensor. This measurement can take place during heating of the heating element after starting up the endoscope, i. e., it can take place after the power-on detection but also without prior power-on detection. Jumps in the temperature curve of the temperature sensor manifest as unexpectedly large temperature jumps. Thus, a threshold for the temperature increase between two successive measurements can be predefined such that a malfunction of the temperature sensor is determined when it is exceeded (positively or negatively). During heating, the monitoring circuit can be energized together with the heating element so that this monitoring can take place without interruptions.

A further embodiment relates to the regular operation of the endoscope when the regular temperature range is reached after heating up. In this case, the monitoring circuit can monitor, during regular operation after activation of the power supply for the heating element, that the temperature measurement of the temperature sensor is not below a predefined lower temperature threshold, wherein the monitoring circuit otherwise determines a malfunction of the temperature sensor. During regular operation, the power supply for the heating element can be cyclically activated and deactivated, whereby the temperature increases, when the power supply is activated, up to an upper threshold, for example 39° C., and is deactivated when the upper threshold is reached, whereby the temperature drops. When a lower threshold, for example 35° C., is underrun, the power supply of the heating element is turned back on. Thereby, the monitoring circuit is also powered again and can determine what temperature the temperature sensor is indicating. If the temperature is below the lower threshold, there is a malfunction of the temperature sensor. This fault detection is not present in the power supplies used to date. If a jump in the temperature measurement to below the lower threshold, for example 34° C., takes place during cooling, a conventional power supply will only detect that further heating is required. The monitoring circuit is in contrast configured to detect this fault.

In one embodiment, the monitoring circuit can store the determination of a malfunction of the temperature sensor in a non-volatile memory and keep the power supply for the heating element interrupted until the memory is purged. The non-volatile memory makes it possible to implement a fault memory that stores, if necessary, also the type of malfunction, and to ensure the blocking function of the monitoring circuit even during a power-off period. The memory is advantageously purged based on an external command or if a subsequent measurement does not confirm the malfunction.

In a further embodiment, the supply unit and/or a central control unit can detect or respectively detect that the power supply for the heating element was interrupted by the monitoring circuit and output a notification hereon. In this way, feedback is provided to users, such as a surgeon who is preparing the endoscope for use in an examination or procedure, or who is performing the examination or procedure. This signals a need for action regarding maintenance or repair of the endoscope.

Such object can also be solved by a heating system of an endoscope, comprising a heating element and a temperature sensor in the distal region of the endoscope and a supply unit outside of the endoscope, the supply unit being connected to the heating element and the temperature sensor, wherein the supply unit is configured to activate and deactivate a power supply for the heating element on the basis of a temperature measurement value ascertained by the temperature sensor using two-state control, wherein a monitoring unit is comprised in the endoscope, such as in a proximal part of the endoscope, which comprises a monitoring circuit powered by the power supply for the heating element, the unit being signal-linked to the temperature sensor and being configured to monitor the temperature measurements of the temperature sensor and to interrupt the power supply to the heating element if a malfunction of the temperature sensor is determined.

The correspondingly expanded heating system comprises the structural components necessary for carrying out the method described above. It thereby embodies the same advantages, properties, and features as the method.

In embodiments, the monitoring unit can comprise a monitoring temperature sensor connected to the monitoring circuit. Thereby, a redundancy is created with regard to the distal temperature sensor of the heating system and a power-on detection is enabled.

In further embodiments, the monitoring circuit can comprise a time member, such as an analog time member, such as a discharging RC member, by which the time of non-powering of the monitoring circuit can be monitored. Furthermore, the monitoring circuit can comprise two separate energy accumulators in embodiments, with a first energy accumulator being chargeable via the power supply for the heating element and a second energy accumulator being chargeable via a conductor from the supply unit to the temperature sensor. Such measures enable the verification of the operating condition that the endoscope is in, namely directly after a longer storage period or in regular operation.

The monitoring circuit can comprise a non-volatile memory for storing malfunctions of the temperature sensor so that it is possible to handle a determined malfunction of the temperature sensor even after a power-off period in such a way that the energizing of the heating element is blocked.

The monitoring circuit can be configured to perform the monitoring, processing, and control steps of a method described above which are assigned to the monitoring circuit, wherein the supply unit and/or a central control unit can be configured to execute the detection and notification described above.

Finally, such object can be solved also by an endoscope system with an endoscope, a supply unit, and a heating system described above. Thereby, the endoscope system also embodies the previously described advantages, properties, and features of the method and the heating system.

BRIEF DESCRIPTION OF THE DRAWING

Further features will become evident from the description of the embodiments together with the claims and the attached drawing. Embodiments can fulfill individual features or a combination of several features.

The embodiments are described below, without restricting the general idea of the invention, based on exemplary embodiments in reference to the drawing, whereby we expressly refer to the drawing with regard to the disclosure of all details that are not explained in greater detail in the text.

FIG. 1 illustrates an endoscope system according to an embodiment.

DETAILED DESCRIPTION

Figure 1:
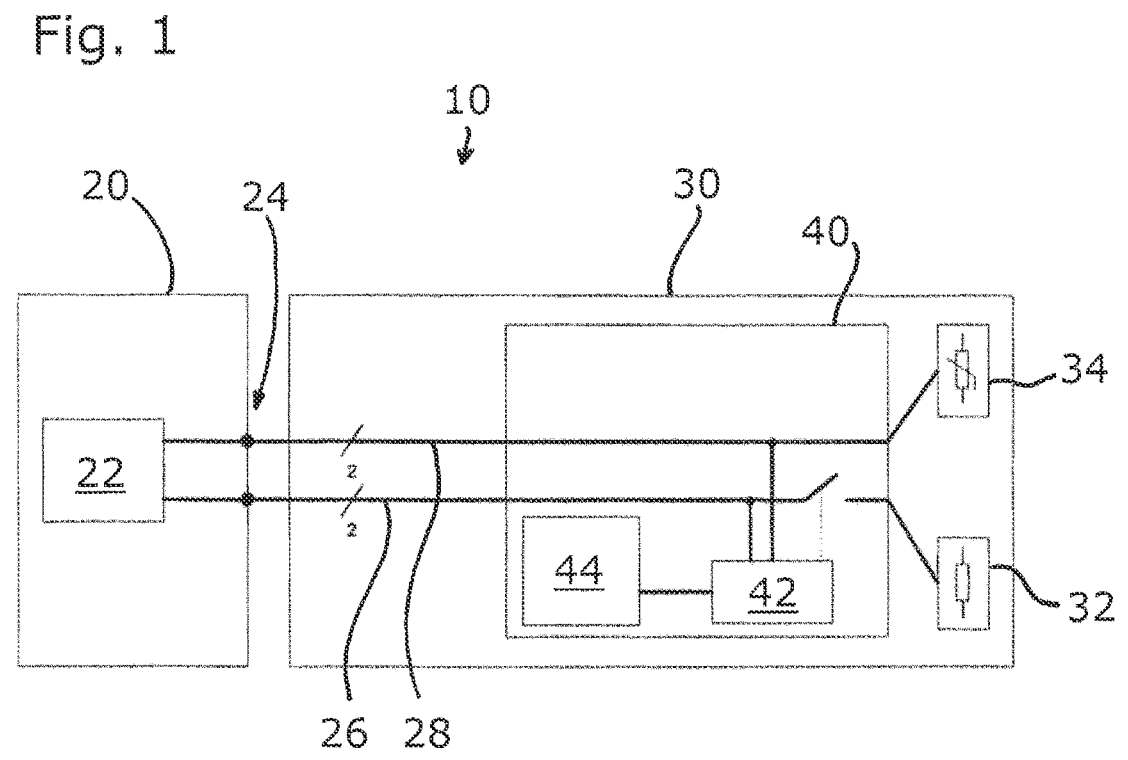
Figure 2:
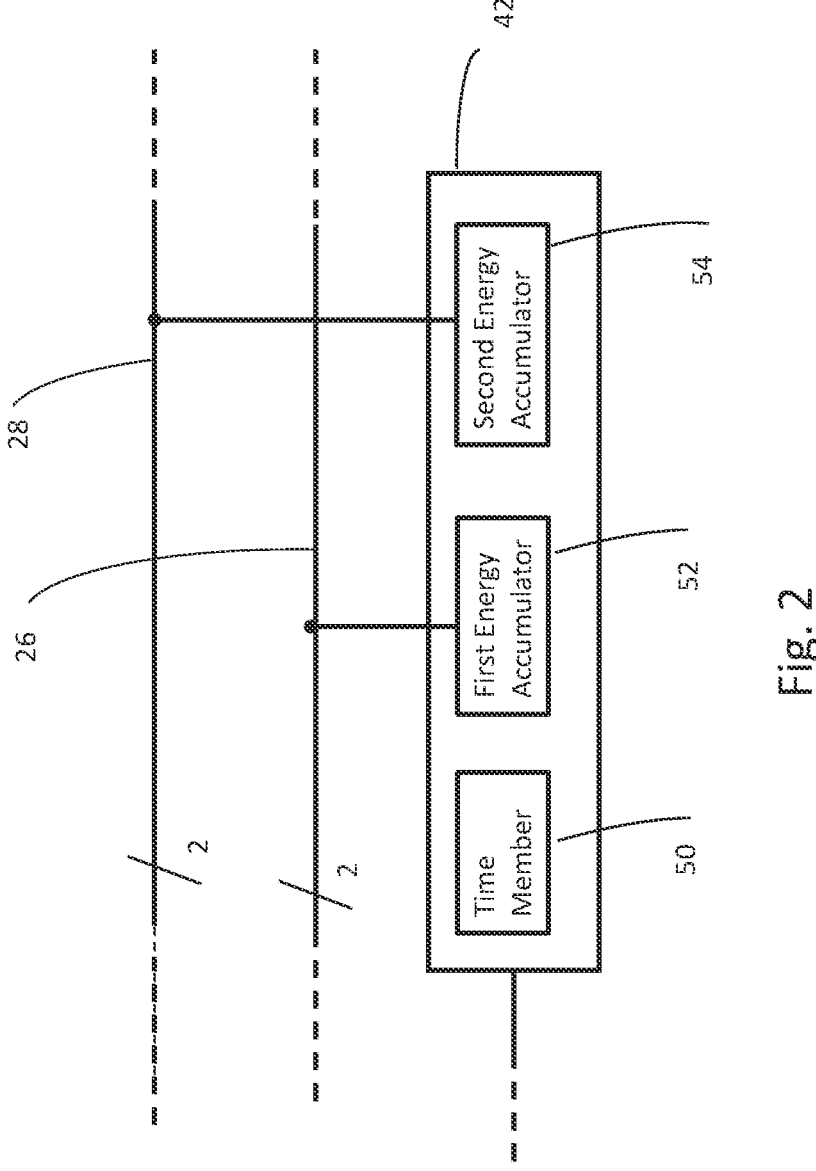
FIG. 2 illustrates an embodiment of the monitoring circuit of FIG. 1.

FIG. 1 schematically shows an endoscope system 10, which comprises an endoscope 30 and a central unit 20, which is configured for the supply and control of the endoscope 30. The central unit 20 comprises a supply unit 22, which is connected via two two-core conductors 26, 28 to a distal heating element 32 and a distal temperature sensor 34, such as a thermistor with a negative temperature coefficient. The heating element 32 can be a heating resistor. The connection is implemented via a coupling interface 24 in which the conductors 26, 28 in the endoscope are connected to external conductors that lead to the supply unit 22. The small numerals 2 below the slashes which cross the two conductors 26, 28 near the connecting lines to the reference signs symbolize the two-core nature of the two conductors 26, 28.

The elements described thus far form the traditional heating system of an endoscope the distal region of which is shown in FIG. 1 on the right. The heating element 32 and the temperature sensor 34 are located in the immediate vicinity of an entrance window (not shown) at the distal end of the endoscope shaft and ensure by heating this region to roughly a body temperature of a patient that the other window does not fog up when the window is introduced into a body cavity of the patient.

The supply unit 22 serves as a controller using a two-state control. For this purpose, it is connected as a constant current source to the temperature sensor 34 via the line 28 and is configured to carry out a temperature measurement via the measurement of the voltage dropping across the temperature sensor 34. Depending on the measured temperature or the measured voltage value corresponding to a temperature value, power to the heating element 32 via line 26 is turned on or off. When an upper threshold is reached, the power supply is deactivated and reactivated when the temperature has dropped to a lower threshold. This is a very simple control which is sufficient for setting the temperature for this purpose.

A monitoring unit 40 is added in the proximal region of the endoscope 30, the monitoring unit comprising a monitoring circuit 42 and a monitoring temperature sensor 44 in the exemplary embodiment shown in FIG. 1. The monitoring circuit 42 is connected to the power supply via the conductor 26, which serves as the power supply for the heating element 32. The monitoring circuit 42 is thus supplied with power parasitically and is thus only powered when the operation of the supply unit 22 is in a state such that the heating element 32 is also intended to be energized. In the cooling phases, the monitoring circuit 42 is not energized either.

The monitoring circuit 42 is moreover connected to the conductor 28, which leads from the supply unit 22 in its function as a constant current source to the temperature sensor 34. Thereby, the monitoring circuit 42 is able to measure the voltage drop across the temperature sensor 34 independently from the external unit and thus to monitor the functioning of the temperature sensor 34.

In the embodiment depicted in FIG. 1, the monitoring unit 40 moreover comprises a monitoring temperature sensor 44 that is connected to the monitoring circuit 42 such that the latter can perform a temperature measurement using the monitoring temperature sensor 44 so long as it is powered. This is the case for example after activation of the endoscope 30, which is already being heated immediately after activation in the distal region. Thus, it is possible to perform a so-called power-on detection during which the surroundings of the temperature sensor 34 and of the monitoring temperature sensor 44 have adapted to the ambient temperature and thus have the same temperature. The temperature measurement with the monitoring temperature sensor 44 is used in this case for verifying the temperature measurement by means of the temperature sensor 34 at room temperature.

Even after activation and during heating of the heating element 32, further monitoring can take place. To this end, successive measurements of the temperature by means of the temperature sensor 34 are performed by the monitoring circuit 42. For this purpose, the monitoring circuit 42 comprises memories for successive temperature measurement values or voltage measurement values, respectively, and a logic, that allow for a comparison of these measurement values and a comparison with thresholds for the maximum permissible differences. This makes it possible to detect jumps in the temperature curve of the temperature sensor 34.

Furthermore, a further monitoring can take place even after regular operation has been achieved, which is made more difficult by the fact that cooling phases occur regularly during regular operation during which neither the heating element 32 nor the monitoring circuit 42 is powered. In this case, the monitoring circuit 42 verifies when the power supply is reactivated whether it was merely a typical cooling phase in that, for example, it is determined that a slowly discharging time member (FIG. 2), for example an RC member, is only slightly discharged, or in that, by means of an energy accumulator (energy storage device) (FIG. 2) of the monitoring circuit 42, which is charged via the conductor 28 to the continually operated temperature sensor 34, it is determined that such accumulator is still charged. Once it is ensured that the case is that of a reactivation after a cooling phase during regular operation, it is determined whether the temperature measured with the temperature sensor 34 is below the lower threshold for the control action or a threshold slightly below that. Such an event is the consequence of a malfunction of the temperature sensor 34.

Furthermore, the central unit 20 and/or optionally the supply unit 22 can be configured to detect if, despite current being supplied by the supply unit 22, the temperature does not change in the distal region of the endoscope. This is an indication that the monitoring circuit 42 has determined a malfunction of the temperature sensor 34 and is blocking the energizing of the heating element 32. If this is detected, a notification or a warning is output that a corresponding event has occurred, and that a maintenance, verification, or repair action of the heating system, such as of the temperature sensor 34, is necessary.

Figure 3:
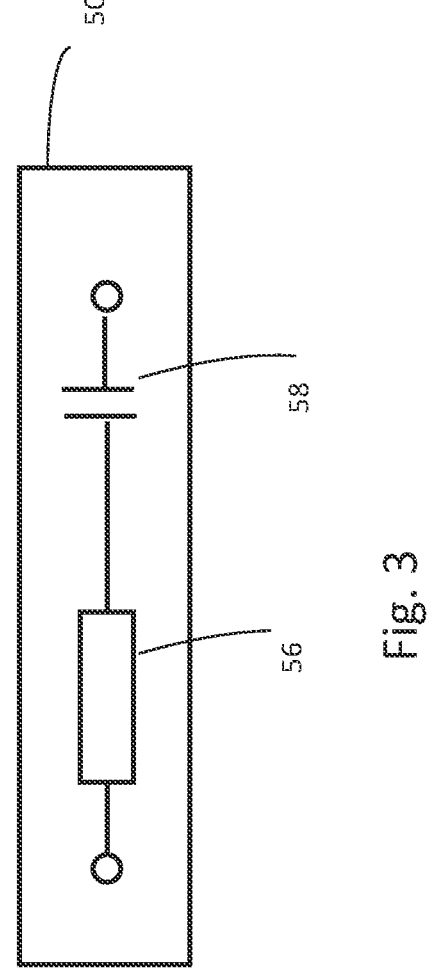
FIG. 3 illustrates an embodiment of the time member of FIG. 2.

Referring now to FIG. 2, there is shown an embodiment of the monitoring circuit 42 having the time member 50, which can be implemented as a discharging RC member, as shown in FIG. 3. As shown in FIG. 3, the discharging RC member can comprise a resistor 56 and a capacitor 58. The time member 50 of FIG. 3 is set to a predetermined voltage and when timing is started, the capacitor 58 starts to discharge over the resistor 56. The decreasing voltage is indicative of the time expired since the start of the discharging. The voltage can be measured at the end clamps shown in FIG. 3.

Referring back to FIG. 2, the monitoring circuit 42 can further comprise a first energy accumulator (first energy storage device) 52 and a second energy accumulator (second energy storage device) 54. The first accumulator 52 is coupled to the supply unit 22 and to the heating element 32, via line 26 (FIG. 1). The second energy accumulator 54 is coupled to the line 28 between the supply unit 22 and the temperature sensor 43. Each of line 26 and line 28, can be twin wired supply lines, this, it is possible to charge the first and the second energy accumulator 52, 54, respectively, by connection to only one of the two lines.

While there has been shown and described what is considered to be preferred embodiments, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

LIST OF REFERENCE SIGNS

10 Endoscope system
20 Central unit
22 Supply unit
24 Coupling interface
26 Two-core electric conductor
28 Two-core electric conductor
30 Endoscope
32 Heating element
34 Temperature sensor
40 Monitoring unit
42 Monitoring circuit
44 Monitoring temperature sensor
50 Time member
52 First energy accumulator
54 Second energy accumulator
56 Resistor
58 Capacitor

What is claimed is:

1. A heating system of an endoscope, the heating system comprising:

a heating element disposed in a distal region of the endoscope;

a temperature sensor disposed in the distal region of the endoscope;

a supply unit disposed outside of the endoscope, the supply unit being connected to the heating element and to the temperature sensor, wherein the supply unit is configured to activate and deactivate a power supply for the heating element on a basis of a temperature measurement value ascertained by the temperature sensor using a two-state control; and a monitoring unit disposed in the endoscope, the monitoring unit comprising a monitoring circuit disposed in the endoscope and powered by the power supply for the heating element; and wherein the monitoring circuit is signal-linked to the temperature sensor and configured to monitor the temperature measurement value of the temperature sensor and to interrupt the power supply to the heating element if a malfunction of the temperature sensor is determined; and the monitoring circuit comprises first and second energy storage devices each configured to store electrical energy, wherein the first energy storage device is configured to be charged via the power supply for the heating element and the second energy storage device is configured to be charged via a conductor from the supply unit to the temperature sensor.

2. The heating system according to claim 1, wherein the monitoring unit is disposed in a proximal part of the endoscope.

3. The heating system according to claim 1, wherein the monitoring unit comprises a monitoring temperature sensor connected to the monitoring circuit.

4. The heating system according to claim 1, wherein the monitoring circuit comprises a time member for monitoring a time during which the monitoring circuit is not energized.

5. The heating system according to claim 4, wherein the time member is an analog time member.

6. The heating system according to claim 5, wherein the analog time member is a discharging RC member.

7. The heating system according to claim 1, wherein the monitoring circuit comprises a non-volatile memory for storing malfunctions of the temperature sensor.

8. An endoscope system comprising:

an endoscope; and the heating system according to claim 1.

* * * * *